(12) United States Patent
Bunke et al.

(10) Patent No.: US 7,032,595 B2
(45) Date of Patent: Apr. 25, 2006

(54) METERING DEVICE FOR ANESTHETICS

(75) Inventors: Claus Bunke, Sereetz (DE); Uwe Bausch, Lübeck (DE); Winfried Kimmig, Gross Grönau (DE); Uwe Bartels, Lübeck (DE); Sven Pasdzior, Travemünde (DE); Bernhard Schaible, Stockelsdorf (DE); Heiko Dickfeld, Gleschedorf (DE); Dirk-Stefan Reichert, Lübeck (DE); Martin Meyer, Lübeck (DE); Matthias Witt, Bad Schwartau (DE); Ralf Dittmann, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 546 days.

(21) Appl. No.: 10/235,761

(22) Filed: Sep. 5, 2002

(65) Prior Publication Data

US 2003/0079745 A1    May 1, 2003

(30) Foreign Application Priority Data

Oct. 26, 2001   (DE) ................................ 101 53 043

(51) Int. Cl.
*A61M 16/00* (2006.01)

(52) U.S. Cl. ........................... 128/203.25; 128/203.12; 128/207.16

(58) Field of Classification Search ................. 128/200.14–200.24, 203.12, 203.13, 203.25, 128/203.26, 203.27, 204.17, 204.18–205.24, 128/207.14–207.18
See application file for complete search history.

(56) References Cited

U.S. PATENT DOCUMENTS 5,243,973 A * 9/1993 Falb et al. ............. 128/203.27

FOREIGN PATENT DOCUMENTS

DE          35 23 948 C2    4/1990

* cited by examiner

*Primary Examiner*—Glenn K. Dawson
(74) *Attorney, Agent, or Firm*—McGlew & Tuttle PC

(57) ABSTRACT

A device for metering anesthetic is provided such that a new anesthetic is immediately available for the metering when the anesthetic is changed. The metering device has an assembly unit that can be removed from the medical apparatus as a module with a reservoir (4) for a liquid anesthetic, an intermediate container (9) arranged downstream of the reservoir (4), a metering gas source (11) connected to the intermediate container (9) and a metering element (14) for anesthetic on the discharge side of the intermediate container (9). An evaporator chamber (15) may be provided for evaporating the metered anesthetic. A connecting device lets through at least anesthetic vapor as an interface between the assembly unit (1) and the medical apparatus (2).

20 Claims, 1 Drawing Sheet

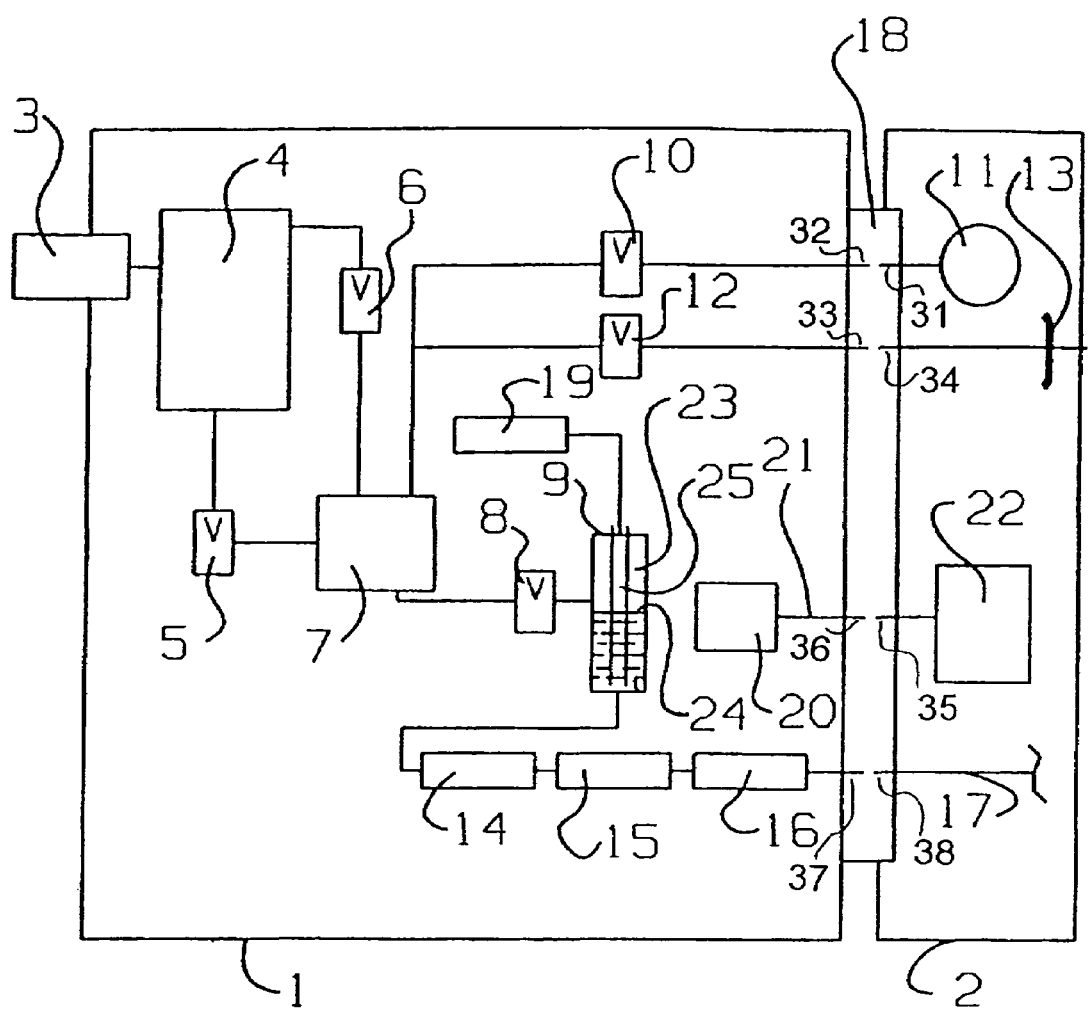

METERING DEVICE FOR ANESTHETICS

FIELD OF THE INVENTION

The present invention pertains to a metering device for anesthetics, which is fastened as a modular assembly unit to a medical apparatus.

BACKGROUND OF THE INVENTION

A device for supplying a medical apparatus with liquid anesthetic has become known from DE 35 23 948 C2. A reservoir of modular design for liquid anesthetic is connected to an anesthesia apparatus in such a way that the reservoir is pushed into the apparatus along a guide. The reservoir is provided with a code, which enables the user to determine which anesthetic is being fed to the anesthesia apparatus by the reservoir being used. In addition, an anesthetic-specific filling device and a filling level indicator are located at the reservoir. In the coupled state of the reservoir, the anesthetic enters a metering device within the anesthesia apparatus via a nonreturn valve and a tapping connection. The tapping connection, which is part of the anesthesia apparatus, opens the nonreturn valve located in the reservoir on coupling, so that the anesthetic can reach the metering device. The desired amount of anesthetic is provided by means of the metering device, which may be designed as a metering pump.

The drawback of the prior-art device is that when the anesthetic is changed, the previous anesthetic is still being metered for some time, because it is still present in the connection line between the tapping connection and the metering device, while the anesthetic to be administered as a new anesthetic will be available only after the residual amount has been used up.

SUMMARY OF THE INVENTION

The basic object of the present invention is to improve a device of this type such that the new anesthetic is immediately available for metering when the anesthetic is changed and that replacement is made possible in a simple manner in case of failure of the metering valve.

According to the invention an anesthetic metering device is provided for anesthetic contained in an assembly unit that can be removed from a medical apparatus as a module. A reservoir for liquid anesthetic is provided. An intermediate container is arranged downstream of the reservoir. A metering pressure source is connected to the intermediate container. A metering element for anesthetic is on the discharge side of the intermediate container. An evaporator chamber is provided for evaporating the metered anesthetic. A connecting device lets through at least anesthetic vapor as an interface between the assembly unit and the medical apparatus.

The advantage of the present invention is essentially that due to the metering element being arranged directly at the assembly unit accommodating the reservoir, the metering element and the reservoir are connected to one another in one assembly unit and the metering element is also replaced as a result during the replacement of the reservoir. It is especially advantageous in the device described in the present invention that anesthetic vapor is released to the medical apparatus, and only the small volume of anesthetic vapor within the pipeline of the medical apparatus needs to the flushed out when the anesthetic is changed. Another advantage is that in case of a defect of the metering element, only a new assembly unit, which contains the metering element, needs to be connected to the medical apparatus, without any appreciable interruption occurring in the operation of the apparatus. The interface between the assembly unit and the medical apparatus can be designed especially advantageously as a plug-type connection, so that the assembly unit can be pushed along a lateral guide directly into a corresponding device mount on the medical apparatus. Due to the plug-type connection, both electric and gas type-specific connections are established when the assembly unit is pushed into the device mount. The plug-type connection may also contain an anesthetic-specific code.

It is also possible to rigidly fasten a plurality of assembly units for different anesthetics at the medical apparatus, so that only the corresponding assembly unit is put into operation depending on the desired anesthetic. The assembly units then need to be removed from the medical apparatus for maintenance purposes only.

The maintenance of the metering element is also substantially simplified by the fastening described in the present invention within the assembly unit, because the metering element can be maintained and tested independently from the medical apparatus.

It is especially advantageous in the device described in the present invention that the reservoir and the intermediate container, from which the metering is performed, are designed as separate assembly units. It is possible as a result to design the reservoir as a large-volume container, which receives the anesthetic under ambient pressure conditions from a storage cylinder. By contrast, the intermediate container is pressurized by means of a metering pressure source to ensure that the admission pressure necessary for the metering element is present. The anesthetic liquid can then be filled in to the intermediate container as needed. In addition, the anesthetic is prevented from boiling within the intermediate container due to the overpressure within the intermediate container. It is especially useful to set the pressure within the intermediate container such that it is about 100 mbar to 300 mbar above the vapor pressure of the anesthetic. It is achieved as a result that only liquid anesthetic will reach the metering element and metering from the vapor phase is avoided.

The metering pressure source advantageously comprises a compressed gas source, which is connected to a storage tank located in the line between the reservoir and the intermediate container. The storage tank is used here as a buffer volume between the reservoir and the intermediate container by the storage tank being first uncoupled from the intermediate container by means of a valve in order to subsequently fill it up with anesthetic liquid from the reservoir. The storage tank is then separated from the reservoir and overpressure is admitted to it from the compressed gas source, so that the intermediate container, which is under pressure, can then be filled up from the storage tank. It is achieved as a result that the reservoir, in which a large liquid volume is present, on the order of magnitude of about 300 mL, is always pressureless, whereas overpressure conditions are present in the storage tank and in the intermediate container only, which together have a volume of about 50 mL.

The metering element is advantageously designed as a metering valve in the form of an injection valve, as is known from the motor vehicle technology. Due to the injection valve being actuated by means of a pulse-pause-modulated control signal, a broad range of variation of the amount of anesthetic being metered can be obtained. The injection valve receives electric control signals from a microprocessor computer within the assembly unit, and it is opened or closed with these signals. As an alternative to an injection valve, it is also possible to use a micrometering pump. As an alternative to electrically operated valves, it is also possible to use pneumatically actuated metering valves or pumps.

The pressure in the intermediate container, which is decisive for the metering of the anesthetic, is determined by means of a pressure-measuring means. This pressure determination is used to monitor the metering pressure, on the one hand, and, on the other hand, the pressure measured may also be included in the calculation of the volume of anesthetic metered for correction purposes, so that the accuracy of the metering can be increased as a result.

The anesthetic vapor being metered is monitored by means of a volume flow sensor on the discharge side of the evaporator chamber, and the metered and measured volumes are compared with one another within the microprocessor computer, so that possible deviations can be immediately recognized and the metering can also be completely interrupted if necessary.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:
The only FIGURE is a schematic view showing a metering device of modular design for anesthetic at a medical apparatus.

DESCRIPTION OF THE PREFERRED EMBODIMENT

Referring to the drawings in particular, the only FIGURE schematically shows a metering device 1 of modular design for anesthetic at a medical apparatus 2. In the metering device 1, liquid anesthetic is fitted into a reservoir 4 via a filling device 3. The reservoir 4 is connected to a storage tank 7 via a filling valve 5 and a ventilating valve 6. The connection to an intermediate container 9 is established via a valve 8. Via a valve 10, the storage tank 7 is connected to a compressed gas source 11. A ventilating valve 12 establishes the connection to an anesthetic gas discharge line 13. The liquid anesthetic from the intermediate container 9 is sent by means of an injection valve 14 into a heated evaporator chamber 15, and it then enters a line 17 of the medical apparatus 2 as an anesthetic vapor via a volume flow sensor 16. The coupling between the metering device 1 and the medical apparatus 2 is established via a detachable connecting device or connecting means 18, in the form of a plug-type connection. The plugs 32, 33, and 37 of the metering device 1 and plugs 31, 34 and 38 of medical apparatus 2 are inserted in associated sockets of the connecting means 18 forming fluid connections (gas-carrying interconnections). The plug 36 of the metering device 1 and the plug 35 of the medical apparatus 2 are inserted in associated sockets of the connecting means 18 providing an electrical connection (current carrying interconnection). The metering pressure in front of the injection valve 14 is measured by means of a pressure-measuring means 19 at the intermediate container 9.

All control and monitoring tasks of the metering device 1 are performed by a microprocessor computer 20, which actuates both the valves 5, 6, 8, 10, 12 as well as the injection valve 14 and processes the measured values of the pressure-measuring means 19 and of the volume flow sensor 16. The microprocessor computer 20 is in connection with a control unit 22 of the medical apparatus 2 via a data line 21.

The metering device 1 according to the present invention operates as follows: Anesthetic liquid is filled into the reservoir 4 via the filling device 3. The filling device 3 is then closed. After opening the valves 5, 6, anesthetic flows into the initially pressureless storage tank 7. Anesthetic now enters the storage tank 7 via the filling valve 5 and the pressure equalization takes place via the ventilating valve 6. When the storage tank is completely filled, the valves 5, 6 close and the storage tank 7 is connected to the compressed gas source 11 by opening the valve 10. The ventilating valve 12 is now closed. The anesthetic is delivered by the pressure prevailing in the storage tank 7 into the intermediate container 9, where a certain liquid level 24 becomes established below a gas volume 23. The liquid level 24 is monitored by means of a filling level detector 25. If the liquid level 24 drops below a certain minimum level, anesthetic is filled up from the storage tank 7 by opening the valve 8 until a minimum level is reached in the intermediate container 9. The valve 8 then closes and the storage tank 7 can again be filled up from the reservoir 4. The valve 10 must have been closed before for this purpose in order to uncouple the compressed gas source 11 from the storage tank 7, and the pressure relief of the storage tank 7 takes place via the ventilating valve 12 into the anesthetic gas discharge line 13. The valves 5, 6 can then again be opened for refilling. The volumes of the containers 4, 7, 9 are selected to be such that the storage tank 4 has a capacity of about 300 mL and can thus receive a commercially available cylinder volume of anesthetic, while the storage tank 7 has a filling volume of about 5 mL, and the intermediate container 9 has a volume of 40 mL. As a result, the pressure from the compressed gas source 11 is admitted to only a comparatively small container volume, and only a small residual amount of anesthetic will remain in the apparatus when the reservoir 4 is possibly emptied.

While specific embodiments of the invention have been shown and described in detail to illustrate the application of the principles of the invention, it will be understood that the invention may be embodied otherwise without departing from such principles.

What is claimed is:

1. An anesthetic assembly unit that can be removed from a medical apparatus as an anesthetic metering device module, the unit comprising:
   a liquid anesthetic reservoir;
   an intermediate container arranged downstream of said reservoir;
   a metering pressure source connected to said intermediate container;
   a metering element for metering anesthetic on a discharge side of the intermediate container;
   an evaporator chamber for evaporating metered anesthetic; and
   a connecting means providing an interface between the assembly unit and the medical apparatus for a gas-carrying interconnection between the metering device module and the medical apparatus.

2. A device in accordance with claim 1, further comprising a storage tank, wherein the metering pressure source is a compressed gas source connected to said storage tank located between the reservoir and the intermediate container.

3. A device in accordance with claim 1, wherein the metering element is one of a injection valve and a micrometering pump.

4. A device in accordance with claim 1, further comprising: a pressure-measuring device provided for determining the pressure in said intermediate container.

5. A device in accordance with claim 1, further comprising: a volume flow sensor arranged on a discharge side of said evaporator chamber.

6. A metering device for anesthetic, comprising an assembly unit that can be removed from a medical apparatus as a module with a reservoir for liquid anesthetic, an intermediate container arranged downstream of said reservoir, a metering pressure source connected to said intermediate container, a metering element metering for anesthetic on a discharge side of the intermediate container, an evaporator chamber for evaporating metered anesthetic, and a connecting device as an interface between the assembly unit arid the medical apparatus, said connecting device letting through at least anesthetic vapor.

7. A device in accordance with claim 6, wherein the metering pressure source is a compressed gas source connected to a storage tank located between said reservoir and said intermediate container.

8. A device in accordance with claim 6, wherein the metering element is an injection valve or a micrometering pump.

9. A device in accordance with claim 6, further comprising: a pressure-measuring device provided for determining the pressure in said intermediate container.

10. A device in accordance with claim 6, further comprising: a volume flow sensor arranged on a discharge side of said evaporator chamber.

11. A method for metering anesthetic, the method comprising the steps of:
    providing an assembly unit that can be removed from a medical apparatus as a module;
    filling a liquid anesthetic into a reservoir of the assembly unit;
    providing an intermediate container and delivering an amount of anesthetic from the reservoir to the intermediate container;
    connecting a metering gas source to the intermediate container;
    metering anesthetic on a discharge side of the intermediate container;
    evaporating the metered anesthetic; and
    delivering the evaporated metered anesthetic as anesthetic vapor from the unit to the medical apparatus via a connector.

12. A method for metering anesthetic in accordance with claim 11, further comprising the intermediate step of transferring anesthetic from the reservoir to a storage tank prior to delivering the anesthetic to the intermediate container.

13. A method for metering anesthetic in accordance with claim 11, further comprising the step of utilizing one of a injection valve and a micrometering pump to meter the anesthetic.

14. A method for metering anesthetic in accordance with claim 11, further comprising the step of measuring pressure in the intermediate container.

15. A metering device for anesthetic that can be removed from a medical apparatus, the device comprising:
    a reservoir for receiving anesthetic;
    a filling device for introducing the anesthetic into said reservoir;
    reservoir valving for controlling movement of the anesthetic from said reservoir to a storage tank;
    a pressure source with gas valving for pressurizing said storage tank with a gas;
    a blow off valve for controlling movement of the anesthetic from said storage tank to an intermediate container;
    a flow metering element for metering flow of the anesthetic from said intermediate container to an evaporator chamber; and
    a flow sensor for measuring flow of the anesthetic from said evaporator chamber to an anesthetic feed line.

16. A metering device in accordance with claim 15, wherein the flow metering element is one of an injection valve and a micometering pump.

17. A metering device in accordance with claim 15, further comprising:
    a pressure measuring device for determining pressure m said intermediate container.

18. A metering device in accordance with claim 15, wherein said evaporator chamber is heated.

19. A metering device in accordance with claim 15, further comprising:
    a connection means for connecting the metering device to the medical apparatus.

20. A metering device in accordance with claim 15, further comprising:
    a microprocessor for interfacing with the medical apparatus and controlling the metering device.

* * * * *